United States Patent [19]

van Loveren et al.

[11] Patent Number: 4,572,796
[45] Date of Patent: Feb. 25, 1986

[54] 1,1,4,7-TETRAMETHYL-3-INDANONE, PRODUCT PRODUCED THEREBY AND ORGANOLEPTIC USES THEREOF

[75] Inventors: Augustinus G. van Loveren, Rye Brook, N.Y.; Mark A. Sprecker, Sea Bright, N.J.; Patrick Whelan, Matawan, N.J.; Marie R. Hanna, Hazlet, N.J.

[73] Assignee: International Flavors & Fragrances Inc., New York, N.Y.

[21] Appl. No.: 671,407

[22] Filed: Nov. 14, 1984

Related U.S. Application Data

[63] Continuation-in-part of Ser. No. 613,570, May 24, 1984, Pat. No. 4,532,357.

[51] Int. Cl.$^4$ .................... C07C 49/69; A61K 7/46
[52] U.S. Cl. .................... 252/522 R; 568/327; 568/321; 252/86; 252/89.1; 252/108
[58] Field of Search .................... 568/321, 327; 252/522 R, 86, 89.1, 108

[56] References Cited

U.S. PATENT DOCUMENTS

| | | | |
|---|---|---|---|
| 1,789,924 | 1/1931 | Binapfl et al. | 568/321 |
| 2,912,462 | 11/1959 | Goldstein | 568/327 |
| 3,078,319 | 2/1963 | Wood | 568/327 |
| 3,422,147 | 1/1969 | Fenton | 568/321 |
| 3,509,215 | 4/1970 | Wood et al. | 568/327 |
| 3,847,993 | 11/1974 | Hall | 568/327 |
| 4,175,098 | 11/1979 | Miyukami et al. | 568/321 |

FOREIGN PATENT DOCUMENTS 57-53768  6/1982  Japan .................... 568/327

OTHER PUBLICATIONS

Hanns et al, Chem. Abst., vol. 77, #101284r (1972).
Ferrero et al, Chem. Abst., vol. 54, #14202g (1960).
Buu–Hoi et al, Bull. Chem. Soc. Fr., pp. 812–816 (1947).
Hoy et al, Can. J. Chem., vol. 43, pp, 1306–1317 (1965).
Arctdnder, "Perfume & Flavor Chemicals (Aroma Chemicals)", vol. II, Monograph, 1791 (1969).

Primary Examiner—James H. Reamer
Attorney, Agent, or Firm—Arthur L. Liberman

[57] ABSTRACT

Described is a process for producing 1,1,4,7-tetramethyl-3-indanone defined according to the structure:

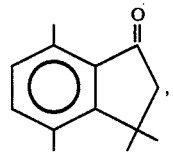

the 1,1,4,7-tetramethyl-3-indanone per se and organoleptic uses thereof in augmenting or enhancing the aroma of perfume compositions, perfumed articles and colognes.

6 Claims, 8 Drawing Figures

FIG. 2

GLC PROFILE FOR EXAMPLE II. CRUDE

FIG. 1

GLC PROFILE FOR EXAMPLE I.

FIG. 5 NMR SPECTRUM FOR EXAMPLE I.

FIG. 6
IR SPECTRUM FOR EXAMPLE I.

FIG. 7

NMR SPECTRUM FOR EXAMPLE I.

1,1,4,7-TETRAMETHYL-3-INDANONE, PRODUCT PRODUCED THEREBY AND ORGANOLEPTIC USES THEREOF

This application is continuation-in-part of application for U.S. Letters Patent Ser. No. 613,570 filed on May 24, 1984 now U.S. Pat. No. 4,532,357.

BACKGROUND OF THE INVENTION

The instant invention relates to 1,1,4,7-tetramethyl-3-indanone defined according to the structure:

a process for preparing same and uses of same in augmenting or enhancing the aroma of perfume compositions, perfumed articles and colognes.

Inexpensive chemical compounds which can provide ambery, leathery, wood, fig-like and honey aromas with tobacoo and hay-like topnotes are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to fine synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Bicyclic ketones are known for use in perfumery in the prior art. Thus, Arctander, "Perfume and Flavor Chemicals (Aroma Chemicals)" 1969, at monograph number 1791 and U.S. Pat. No. 2,912,462 issued on Nov. 10, 1959 discloses the compound having the structure:

as having a dry, woody, amber-like and somewhat orris-like aroma. The compound having the structure:

is commercially sold as "KETONE BD-9".

The compound having the structure:

wherein one of the dashed lines represents a carbon-carbon double bond and the other of the dashed lines represents a carbon-carbon single bond is disclosed as being useful in perfumery (having a wood or ambergris aroma) in Japanese Published Patent No. 57-53768 assigned to the Takasago Perfumery Company.

The compound having the structure:

is disclosed as being useful in perfumery in U.S. Pat. No. 3,847,993 issued on Nov. 12, 1974. This compound is indicated to be produced using the compound having the structure:

as a precursor according to the reaction:

The compound having the structure:

is disclosed as being useful in perfumery by Ferrero and Heig, Helv. Chim. Act. Volume XVII, Fasc. VI (1959) Number 228 at page 2111. This compound having the structure:

is produced from the compound having the structure:

which is indicated to be an intermediate. Furthermore, in Ferrero and Heig, the compound having the structure:

is indicated to be an intermediate for producing acylated indanes from the compound having the structure:

The compound having the structure:

is indicated as compound XXIX. The compound having the structure:

is indicated as compound XXVIII in Example C-3 at page 2119 of Ferrero and Heig.

Furthermore, the reaction:

wherein R is lower alkyl such as methyl is disclosed in U.S. Pat. No. 3,078,319 issued on Feb. 19, 1963 wherein it is indicated that the resulting indanes may be acylated.

In addition, the use of cobalt acetate bromide and oxygen for the production of ketones is shown by Hay, et al, in the Canadian Journal of Chemistry, 43,1306 (1965). In this process, tetralin is oxidized to the corresponding ketone, that is α-tetralone.

Nothing in the prior art, however, indicates the unexpected, unobvious and advantageous properties of the 1,1,4,7-tetramethyl-3-indanone having the structure:

Furthermore, nothing in the prior art describes the process for preparing such 1,1,4,7-tetramethyl-3-indanone according to the reaction sequence:

and

BRIEF DESCRIPTION OF THE DRAWINGS

FIG. 3 is the NMR spectrum for the compound having the structure:

prepared according to Example II (Conditions: Field strength: 100 MHz; solvent: CFCl₃).

FIG. 4 is the infra-red spectrum for the compound having the structure:

prepared according to Example II.

FIG. 5 is the NMR spectrum for the compound having the structure:

produced according to Example V (the product of the peak indicated by reference numeral 10 on FIG. 1).

FIG. 6 is the infra-red spectrum for the compound having the structure:

produced according to Example I (peak 10 on FIG. 1).

FIG. 7 is the NMR spectrum for the mixture of compounds having the structures:

and produced according to Example I (peak 11 of GLC profile of FIG. 1).

FIG. 8 is the infra-red spectrum for the mixture of compounds having the structures:

and produced according to Example I (peak 11 of FIG. 1, the GLC profile of the crude reaction product of Example I).

DETAILED DESCRIPTION OF THE DRAWINGS

Figure 1:
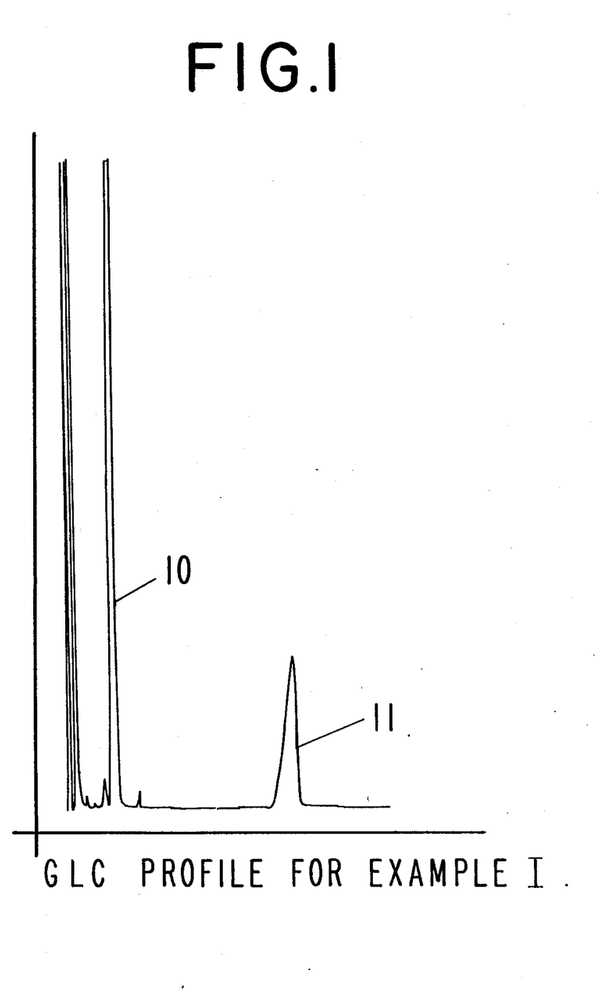
FIG. 1 is the GLC profiled for the crude reaction product of Example I containing the compounds having the structures.

FIG. 1 is the GLC profile for the reaction product of Example I containing the compounds having the structures:

and

Figure 2:
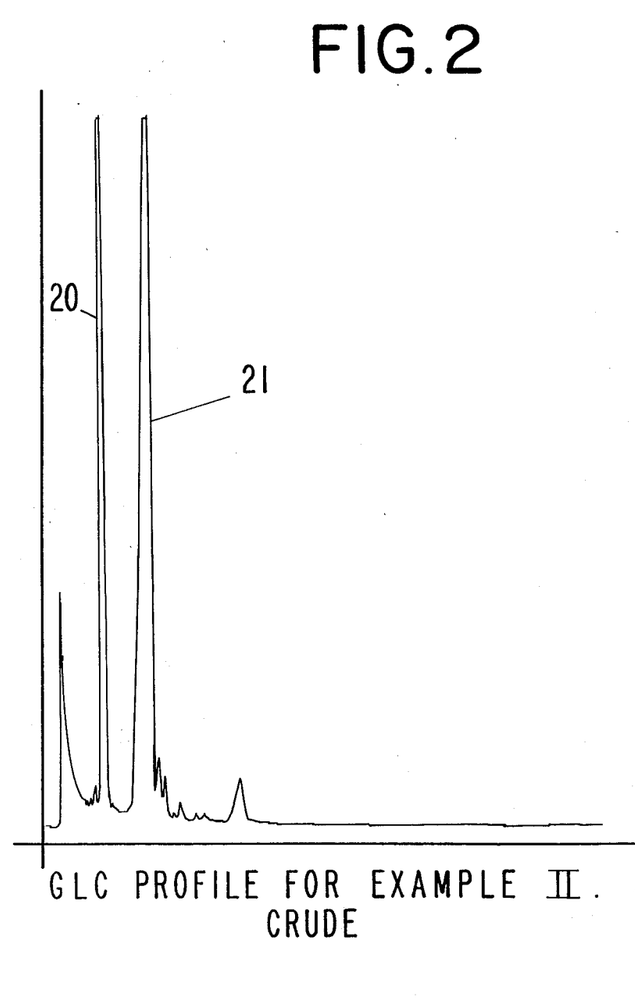
FIG. 2 is the GLC profile for the reaction product of Example II containing the compounds having the structures.

The peak indicated by reference numeral 10 is the peak for the compound having the structure:

The peak indicated by reference numeral 11 is the peak for the mixture of compounds having the structures:

FIG. 2 is the GLC profile for the crude reaction product of Example II containing the compounds having the structures:

The peak indicated by reference numeral 20 is the peak for the compound having the structure:

The peak indicated by reference numeral 21 is the peak for the compound having the structure:

THE INVENTION

The present invention provides the 1,1,4,7-tetramethyl-3-indanone having the structure:

The composition of matter of our invention produced according to the process of our invention is capable of augmenting or enhancing or providing ambery, leathery, woody, fig-like and honey aromas with tobacco and hay-like topnotes to perfume compositions, colognes and perfumed articles (e.g., solid or liquid anionic, cationic, nonionic or zwitterionic detergents, fabric softener articles, dryer-added fabric softener articles, fabric softener compositions, cosmetic powders, hair preparations, perfumed polymers and the like).

The 1,1,4,7-tetramethyl-3-indanone of our invention is first prepared by reacting para-xylene with isoprene in the presence of an acetic catalyst, e.g., sulfuric acid, to form the tetramethyl indane compound having the structure:

according to the reaction:

The parameters for this reaction are set forth in U.S. Pat. No. 3,078,319 issued on Feb. 19, 1963, the specification for which is incorporated by reference herein.

The resulting indane derivative defined according to the structure:

is then reacted with oxygen using an appropriate catalyst in order to form the 1,1,4,7-tetramethyl-3-indanone of our invention defined according to the structure:

according to the reaction:

The reaction temperature may be in the range of from about 25° C. up to about 150° C. at a pressure of from about 1 atmosphere up to about 10 atmospheres. The reaction takes place in the presence of a solvent such as acetic acid or benzene or in the absence of a solvent. The reaction takes place using a catalyst such as cobalt naphthenate, cobalt acetoacetate or cobalt diacetate. Other transition metals (e.g., chromium, maganese or copper) catalysts may also be used in these transition metal catalysts of the standard oxidation catalysts.

The reaction may also be carried out using air rather than oxygen. When using air as a reactant, the indane derivative having the structure:

is charged into an autoclave with the appropriate catalyst preferably a cobalt salt, such as cobalt acetoacetate.

The amount of catalyst used in the oxidation reaction may be from about 0.1% up to about 1% by weight of the reaction mass.

When using air, the air is introduced into the autoclave at a set velocity, preferably about 500 cc per minute. Preferably, when using air, the reaction pressure may vary from about 50 up to about 500 psig, more preferably between about 100 and 200 psig.

The 1,1,4,7-tetramethyl-3-indanone prepared in accordance with the process of our invention and one or more auxiliary perfume ingredients, including, for example, alcohols, aldehydes, ketones other than the 1,1,4,7-tetramethyl-3-indanone of our invention, terpenic hydrocarbons, nitriles, esters, lactones, natural essential oils and synthetic essential oils may be admixed so that the combined odors of the individual components produce a pleasant and desired fragrance, particularly and preferably in the leathery, amber, spicy and "Chypre" fragrances. Such perfume compositions usually contain:

(a) the main note or the "bouquet" or foundation stone of the composition;
(b) modifiers which round-off and accompany the main note;
(c) fixatives which include odorous substances which lend a particular note to the perfume throughout all stages of evaporation and substances which retard evaporation; and
(d) topnotes which are usually low boiling fresh smelling materials.

In perfume compositions, it is the individual components which contribute their particular olfactory characteristics, however, the overall sensory effect of the perfume composition will be at least the sum total of the effects of each of the ingredients. Thus, the 1,1,4,7-tetramethyl-3-indanone prepared in accordance with the process of our invention can be used to alter, modify or enhance the aroma characteristics of a perfume composition, for example, by utilizing or moderating the olfactory reaction contributed by another ingredient in the composition.

The amount of the 1,1,4,7-tetramethyl-3-indanone prepared in accordance with the process of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the 1,1,4,7-tetramethyl-3-indanone prepared in accordance with the process of our invention or even less (e.g., 0.005%) can be used to impart, augment or enhance leathery, ambery, woody and honey aromas with tobacco and hay-like topnotes to soaps, cosmetics, anionic, cationic, nonionic or zwitterionic detergents, fabric softener compositions, fabric softener articles, microporporous polymers, particularly acrylic resins, polyethylenes and other products. The amounts employed can range up to 70% of the fragrance components and will depend on considerations of cost, nature of the end product, the effect desired on the finished product and the particular fragrance sought.

The 1,1,4,7-tetramethyl-3-indanone prepared in accordance with the process of our invention is useful (taken alone or together with other ingredients in perfume compositions) as an olfactory component in detergents and soaps, space odorants and deodorants, perfumes, colognes, toilet waters, bath preparations such as creams, deodorants, hand lotions and sunscreens; powders such as talcs, dusting powders, face powders, microporous "perfumed" slow release polymers and the like.

When used as (an) olfactory component(s) in perfumed articles, as little as 0.005% of the 1,1,4,7-tetramethyl-3-indanone prepared in accordance with the process of our invention will suffice to impart, augment or enhance leathery, amber, woody, honey and fig-like aromas with tobacco and hay-like topnotes. Generally, no more than 6% of the 1,1,4,7-tetramethyl-3-indanone of our invention based on the ultimate end product is required in the perfumed article. Accordingly, the range of use of the 1,1,4,7-tetramethyl-3-indanone of our invention in perfumed articles, per se, is from about 0.005% up to about 6% by weight based on the perfumed article.

In addition, the perfume composition or fragrance composition of our invention can contain a vehicle or carrier for the 1,1,4,7-tetramethyl-3-indanone prepared in accordance with the process of our invention. The vehicle can be a liquid such as a non-toxic alcohol, e.g., ethyl alcohol, and non-toxic glycol, e.g., propylene glycol or the like. The carrier can also be an absorbent solid such as a gum (e.g., gum arabic, guar gum or xanthan gum or combinations thereof) or components for encapsulating the composition (such as gelatin as by coacervation) or polymers such as ureaformaldehyde prepolymers which form a ureaformaldehyde polymer capsule wall around a liquid perfume center.

It will thus be apparent that the 1,1,4,7-tetramethyl-3-indanone prepared in accordance with the process of our invention can be used to alter, modify or enhance sensory properties particularly organoleptic properties such as fragrances of a wide variety of consumable materials.

The following Examples I and II set forth the means for preparing the 1,1,4,7-tetramethyl-3-indanone or our invention. Examples following Example II that is Example III, et seq, set forth illustrations of organoleptic utilities of the 1,1,4,7-tetramethyl-3-indanone of our invention.

All parts and percentages given herein are by weight unless otherwise specified.

EXAMPLE I

Preparation of 1,1,4,7-Tetramethyl Indane

Reaction:

Into a 12 liter reaction vessel equipped with stirrer, thermometer, reflux condenser and heating mantle is placed 64 ml water and 640 grams of concentrated sulfuric acid. The mixture is cooled to 15° C. To the resulting mixture is added 1.59 kilograms (15 moles) of para-xylene while maintaining the temperature of the mixture at 15°-20° C.

Over a period of 4.25 hours while maintaining the reaction mass at 20° C., a mixture of 540 grams (8.0 moles) of isoprene and 1590 grams (15 moles) of para-xylene is added to the reaction mass.

At the end of the 4.25 hour addition period, the reaction mass is stirred for an additional 15 minutes and the organic phase is separated from the aqueous phase. The organic phase is washed with saturated sodium chloride and then neutralized with 50% caustic and 50 grams of triethyl amine.

The resulting product is then distilled on a fractional distillation column yielding the following fractions:

| FRACTION NO. | VAPOR TEMP. (°C.) | LIQUID TEMP. (°C.) | VACUUM mm/Hg. PRESSURE |
|---|---|---|---|
| 1 | 95 | 110 | 5.0 |
| 2 | 88 | 109 | 5.0 |
| 3 | 88 | 120 | 5.0 |
| 4 | 70 | 130 | 0.1 |

FIG. 1 is the GLC profile of the reaction mass prior to distillation.

The peak indicated by reference numeral 10 is the peak for the compound having the structure:

The peak indicated by reference numeral 11 is the peak for the

EXAMPLE II

Preparation of 1,1,4,7-Tetramethyl-3-Indanone

Reaction:

Into a 500 ml "zipperclave" (high pressure autoclave) apparatus is placed 250 grams of the tetramethyl indane having the structure:

prepared according to Example I and, in addition, 1 gram of cobalt acetoacetate. The autoclave is sealed and pressurized to 150 psig at a 500 ml per minute oxygen flow rate. The reaction temperature is maintained at 85°–100° C. over a period of 21 hours.

At the end of the 21 hour period, GLC analysis indicates completion of the reaction. The autoclave is cooled to room temperature, opened and the contents filtered and subjected to distillation on a 2" splash column followed by redistillation on a 12"×1.5" Goodloe column yielding the following fractions:

| FRACTION NO. | VAPOR TEMP. (°C.) | LIQUID TEMP. (°C.) | VACUUM mm/Hg. PRESSURE | REFLUX RATIO R/D |
|---|---|---|---|---|
| 1 | 80/80 | 120/120 | 3/3 | 4:1 |
| 2 | 81 | 126 | 3.0 | 4:1 |
| 3 | 111 | 131 | 3.0 | 4:1 |
| 4 | 114 | 131 | 2.5 | 9:1 |
| 5 | 115 | 133 | 2.5 | 9:1 |
| 6 | 115 | 135 | 2.5 | 9:1 |
| 7 | 115 | 141 | 2.5 | 9:1 |
| 8 | 117 | 157 | 2.5 | 9:1 |
| 9 | 116 | 185 | 2.5 | 9:1 |
| 10 | 116 | 215 | 2.5 | 9:1 |

FIG. 2 is the GLC profile for the crude reaction product prior to distillation.

Figure 3:
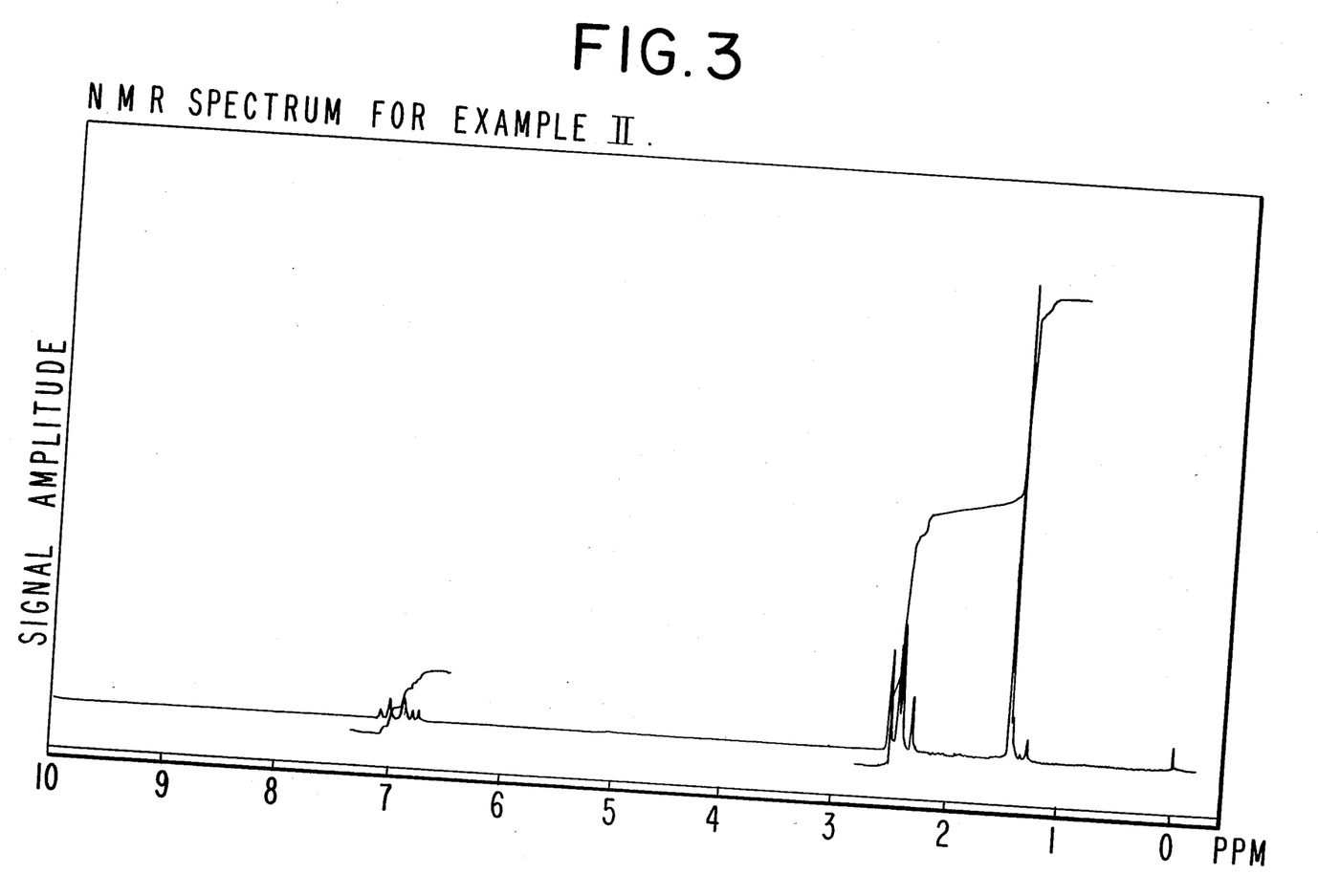

The peak indicated by reference numeral 20 is the peak for the starting material having the structure:

The peak indicated by reference numeral 21 is the peak for the reaction product having the structure:

FIG. 3 is the NMR spectrum for the compound having the structure:

(Conditions: Field strength: 100 MHz; solvent: $CFCl_3$).

Figure 4:
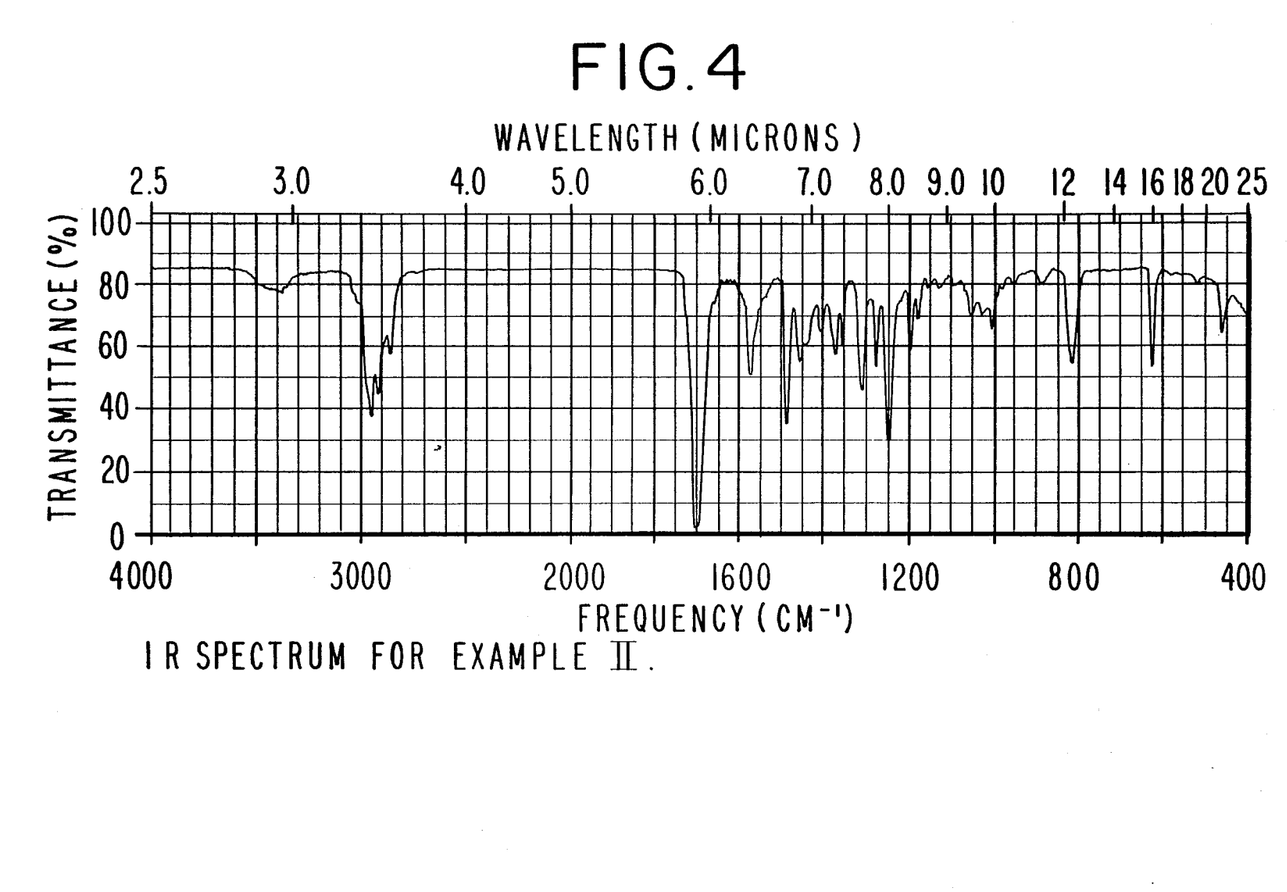
Figure 5:
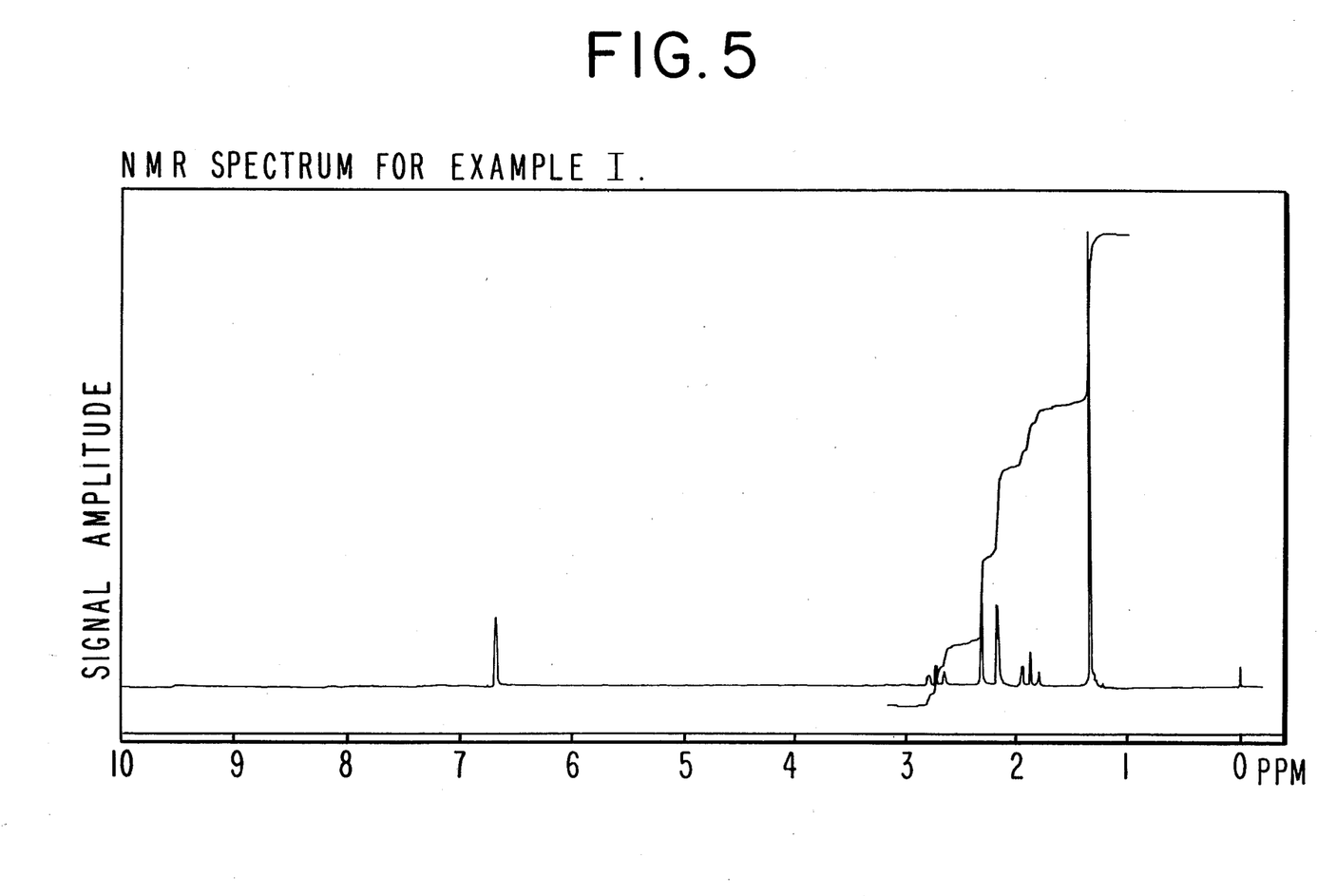
Figure 6:
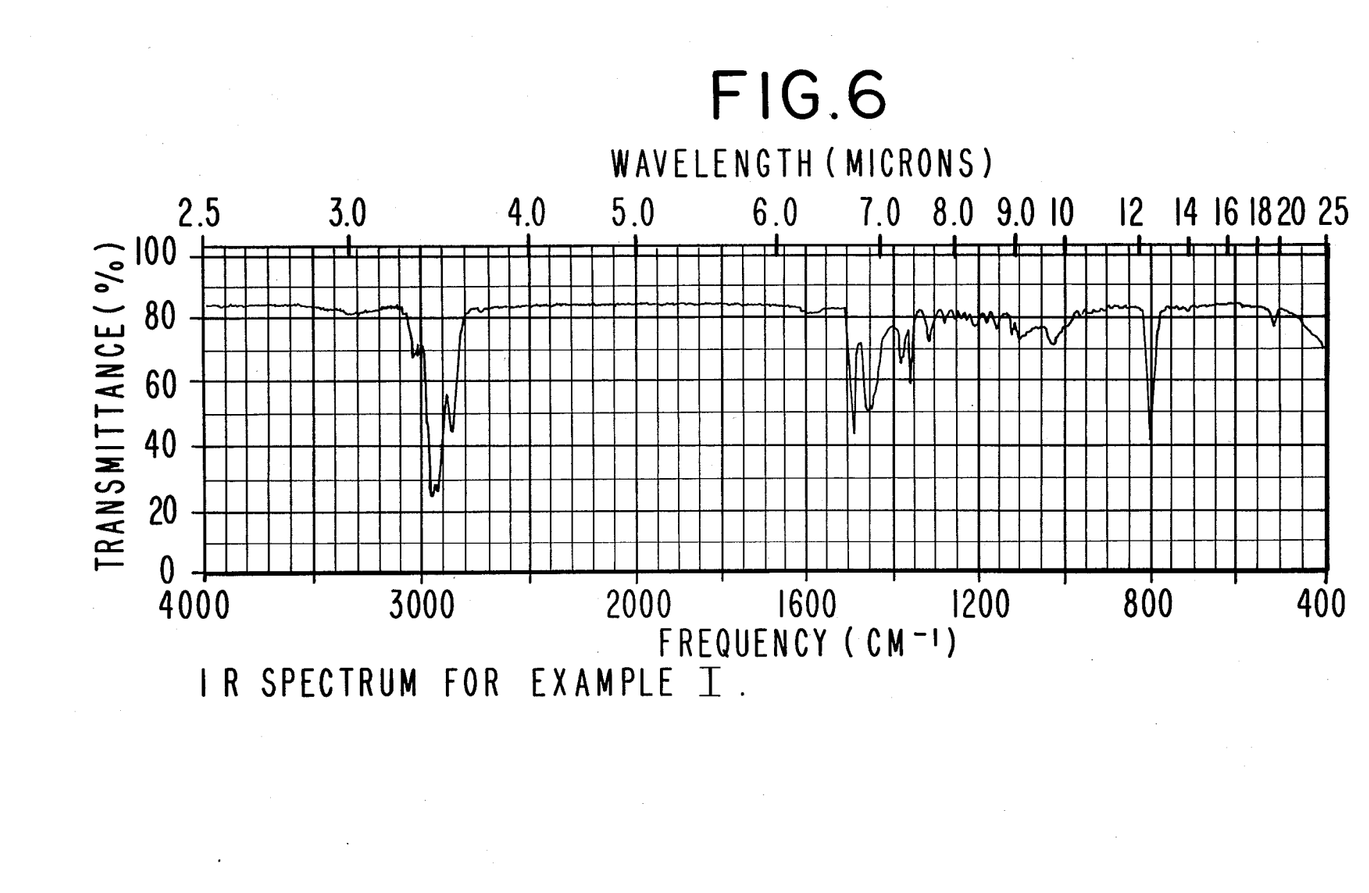
Figure 7:
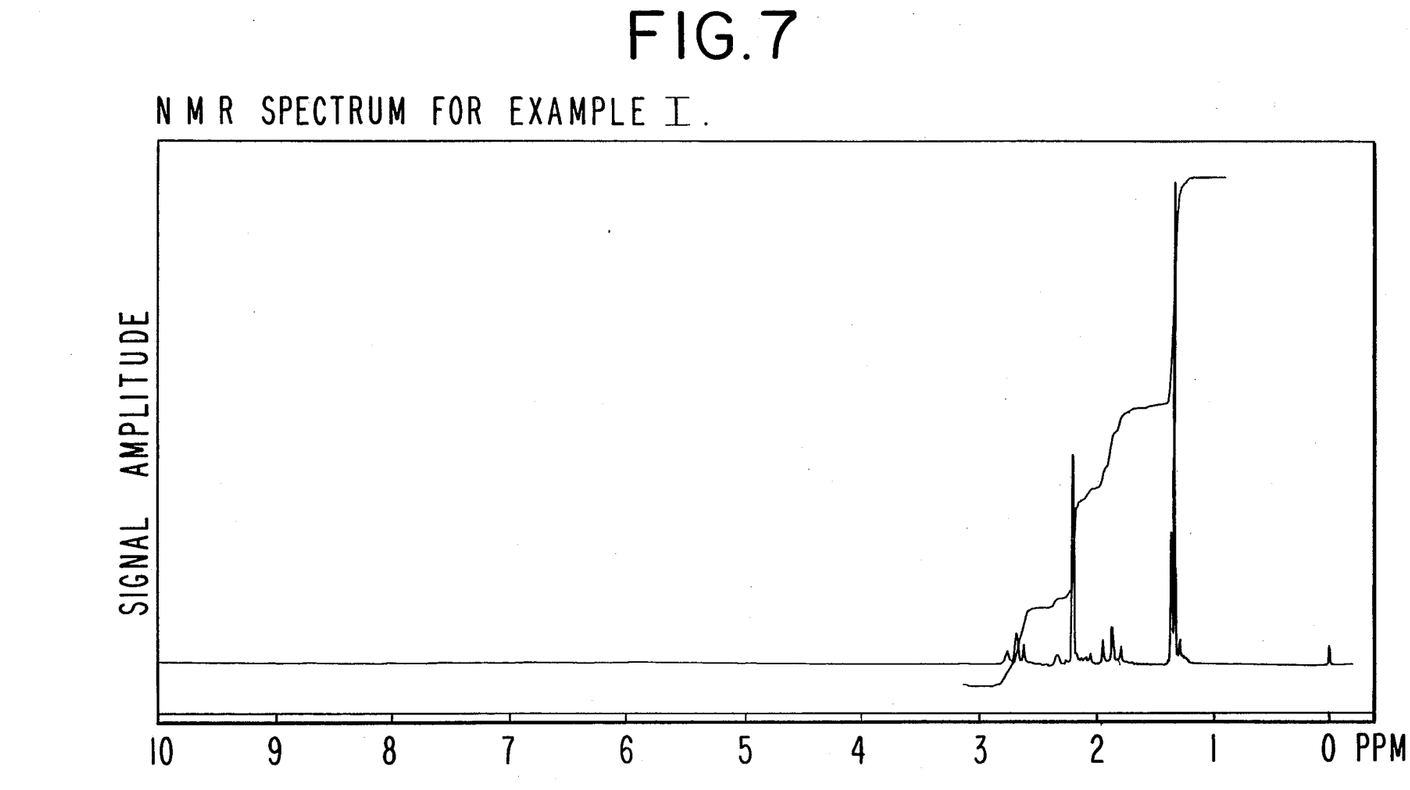
Figure 8:
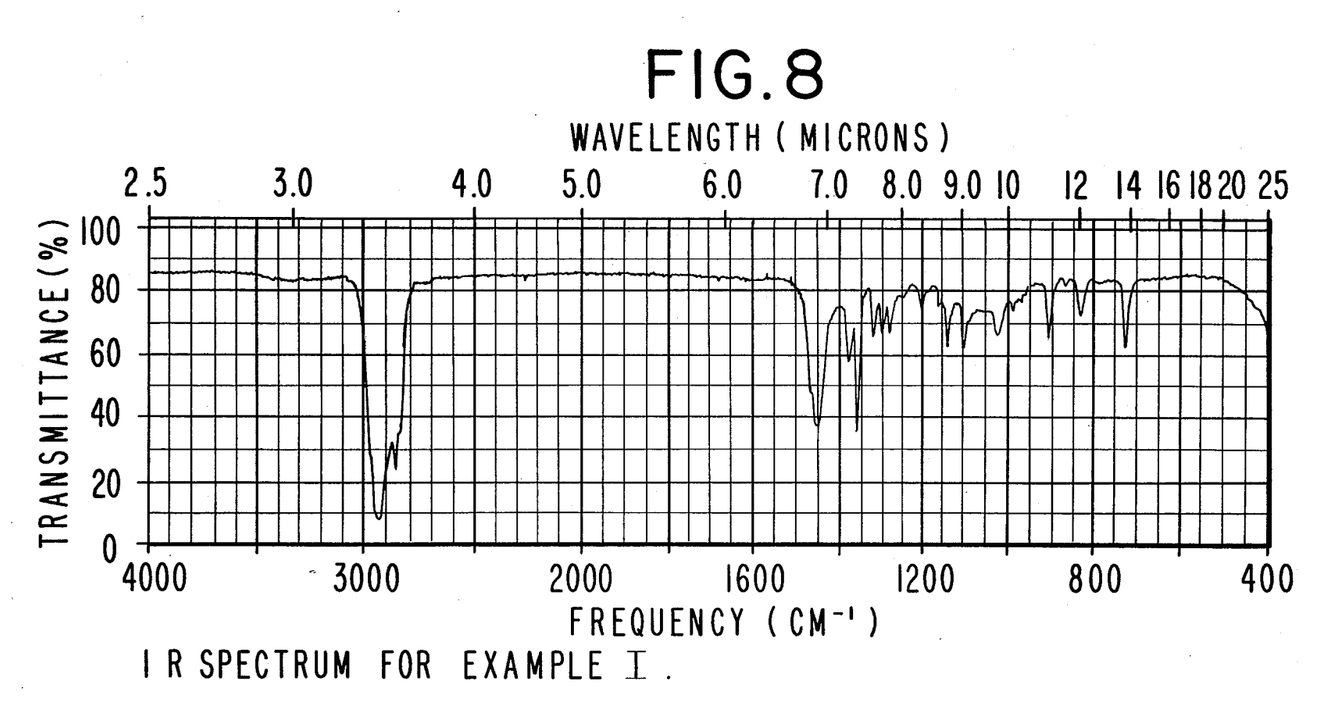

FIG. 4 is the infra-red spectrum for the compound having the structure:

The compound having the structure:

has unexpected, unobvious and advantageous properties: an intense long lasting ambery, leathery, woody, fig-like and honey aroma with tobacco and hay-like topnotes. The compound having the structure:

is ten times as strong as the compound having the structure:

and has a lasting power ten times as long as the compound having the structure:

EXAMPLE III

The following chypre formulation is prepared:

| INGREDIENTS | PARTS BY WEIGHT |
|---|---|
| Musk ambrette | 40.0 |
| Musk ketone | 60.0 |
| Coumarin | 30.0 |
| Oil of bergamot | 150.0 |
| Oil of lemon | 100.0 |
| Methyl ionone | 50.0 |
| Hexyl cinnamic aldehyde | 100.0 |
| Hydroxycitronellal | 100.0 |
| Oil of lavender | 50.0 |
| Texas cedarwood oil | 85.0 |
| Virginia cedarwood oil | 30.0 |
| Oil of sandalwood (East Indies) | 40.0 |
| Isoeugenol | 20.0 |
| Eugenol | 10.0 |
| Benzyl acetate | 30.0 |
| β-phenyl ethyl alcohol | 40.0 |
| α-phenyl ethyl alcohol | 30.0 |
| Oakmoss absolute | 30.0 |
| Vetiver oil (Venezuela) | 25.0 |
| The compound having the structure: | 8.0 |

| INGREDIENTS | PARTS BY WEIGHT |
|---|---|
|  prepared according to Example II | |

The compound having the structure:

imparts to this chypre formulation leathery, amber, fig-like and honey undertones with tobacco and hay-like topnotes. Accordingly, the fragrance can be described as "chypre, with ambery, leathery, woody, fig-like and honey undertones and tobacco and hay-like topnotes".

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| SUBSTANCE | AROMA DESCRIPTION |
|---|---|
| The compound having the structure: | An ambery, leathery, woody, fig-like and honey aroma with tobacco and hay-like topnotes. |
| Perfume composition of Example III | A chypre aroma with ambery, leathery, woody, fig-like and honey undertones and tobacco and hay-like topnotes. |

EXAMPLE V

Preparation of Soap Compositions

One hundred grams of soap chips [per sample] (IVORY ®, produced by the Proctor & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VI

Preparation of Solid Detergent Compositions

Detergents are prepared using the following ingredients according to Example I of Canadian Pat. No. 1,007,948 (incorporated by reference herein):

| INGREDIENT | PERCENT BY WEIGHT |
| --- | --- |
| "Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE VII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and their perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having the aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table I of Example IV, supra.

EXAMPLE VIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| INGREDIENT | PERCENT BY WEIGHT |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table I of Example IV, supra | 0.10 |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE IX

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepen Chemical Company (35.0 weight percent). The resulting mixture is heated to 60° C. and mixed until a clear solution is obtained (at 60° C.). This material is "COMPOSITION A".

Gafquat ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A and COMPOSITION B are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. The 1,1,4,7-tetramethyl-3-indanone having the structure:

in recovered form.

2. A process for augmenting or enhancing the aroma of a consumable material selected from the group consisting of perfume compositions, colognes and perfumed articles comprising the step of adding to said consumable material an aroma augmenting or enhancing quantity of the 1,1,4,7-tetramethyl-3-indanone defined according to claim 1.

3. The process of claim 2 wherein the consumable material is a perfume composition or cologne.

4. The process of claim 2 wherein the consumable material is a perfumed article and the perfumed article is a perfumed polymer.

5. The process of claim 2 wherein the consumable material is a perfumed article and the perfumed article is a solid or liquid anionic, cationic, nonionic or zwitterionic detergent.

6. The process of claim 2 wherein the consumable material is a perfumed article and the perfumed article is a fabric softener composition or a fabric softener article.

* * * * *